United States Patent
Hillbratt et al.

(10) Patent No.: US 12,138,467 B2
(45) Date of Patent: *Nov. 12, 2024

(54) EXTERNAL AND IMPLANTABLE COILS FOR AUDITORY PROSTHESES

(71) Applicant: Cochlear Limited, Macquarie University (AU)

(72) Inventors: Martin Evert Gustaf Hillbratt, Lindome (SE); Werner Meskens, Opwijk (BE); Koen Erik Van den Heuvel, Hove (BE)

(73) Assignee: Cochlear Limited, Maquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/480,737

(22) Filed: Oct. 4, 2023

(65) Prior Publication Data
US 2024/0091543 A1   Mar. 21, 2024

Related U.S. Application Data

(63) Continuation of application No. 17/738,641, filed on May 6, 2022, now Pat. No. 11,826,576, which is a continuation of application No. 16/928,587, filed on Jul. 14, 2020, now Pat. No. 11,344,736, which is a continuation of application No. 15/243,717, filed on Aug. 22, 2016, now Pat. No. 10,744,333.

(60) Provisional application No. 62/208,524, filed on Aug. 21, 2015.

(51) Int. Cl.
*A61N 1/36* (2006.01)
*A61N 1/372* (2006.01)
*A61N 1/378* (2006.01)

(52) U.S. Cl.
CPC ....... *A61N 1/3787* (2013.01); *A61N 1/36036* (2017.08); *A61N 1/36038* (2017.08); *A61N 1/37229* (2013.01)

(58) Field of Classification Search
CPC .............. A61N 1/3787; A61N 1/36036; A61N 1/36038; A61N 1/37229
See application file for complete search history.

(56) References Cited

U.S. PATENT DOCUMENTS

| | | | |
|---|---|---|---|
| 4,696,287 | A | 9/1987 | Hortmann et al. |
| 5,792,217 | A | 8/1998 | Camps et al. |
| 6,272,382 | B1 | 8/2001 | Faltys et al. |
| 6,277,148 | B1 | 8/2001 | Dormer |
| 7,120,501 | B2 | 10/2006 | Boylston et al. |
| 9,132,276 | B2 | 9/2015 | Meskens |
| 9,802,043 | B2 | 10/2017 | von Ilberg et al. |

(Continued)

FOREIGN PATENT DOCUMENTS

WO    WO 2011068822 A2    6/2011

*Primary Examiner* — Paula J Stice
(74) *Attorney, Agent, or Firm* — Edell, Shapiro & Finnan, LLC (57) ABSTRACT

Certain medical devices, such as auditory prostheses, have an implantable portion and an external portion. The implantable portion and external portion each include a transmission/receiver coil that communicates signals between the two portions. The implanted coil is implanted about the ear canal while the external coil is disposed about the pinna or in the ear canal itself. The proximity of the two coils allows for signal transmission between the implantable and external portions.

24 Claims, 13 Drawing Sheets

(56) References Cited

U.S. PATENT DOCUMENTS

| | | |
|---|---|---|
| 10,744,333 B2 | 8/2020 | Hillbratt et al. |
| 2005/0033384 A1 | 2/2005 | Sacha |
| 2010/0030012 A1 | 2/2010 | Meskens |
| 2011/0130622 A1* | 6/2011 | Ilberg ................ A61N 1/36038 600/25 |
| 2015/0283313 A1 | 10/2015 | Huber |
| 2016/0114174 A1 | 4/2016 | Colvin et al. |
| 2018/0028825 A1 | 2/2018 | Leigh |

* cited by examiner

EXTERNAL AND IMPLANTABLE COILS FOR AUDITORY PROSTHESES

CROSS-REFERENCE TO RELATED APPLICATIONS

This application is a continuation of U.S. application Ser. No. 17/738,641, filed May 6, 2022, and issued as U.S. Pat. No. 11,826,576, which is a continuation of U.S. application Ser. No. 16/928,587, filed Jul. 14, 2020, and issued as U.S. Pat. No. 11,344,736, which is a continuation of U.S. application Ser. No. 15/243,717, filed Aug. 22, 2016, and issued as U.S. Pat. No. 10,744,333, which claims the benefit of U.S. Provisional Patent Application No. 62/208,524, filed Aug. 21, 2015, entitled, "EXTERNAL AND IMPLANTABLE COILS FOR AUDITORY PROSTHESES." The disclosures of these priority applications are hereby incorporated by reference in their entirety into the present application.

BACKGROUND

Hearing loss, which can be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient (i.e., the inner ear of the recipient) to bypass the mechanisms of the middle and outer ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Aspects disclosed herein relate to medical devices having an implantable portion and an external portion. The implantable portion and external portion each include a transmission/receiver coil that are used for signal (data and/or power) transmission between the two portions. The implanted coil is disposed about or around the ear canal while the external coil is disposed about the pinna or in the ear canal itself. The proximity of the two coils allows for signal transmission. In certain examples, configuration and location of the implantable and external coils can result in the elimination of magnets in the implantable and external portions.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The coil technologies disclosed herein can be used in conjunction with various types of auditory prostheses, including direct acoustic devices and cochlear implants. Such devices include an implantable portion and an external portion. The implantable portion includes an implantable coil disposed around or about the ear canal and provides a stimulus to the recipient. The external portion receives sound, processes sound signals, and sends signals to the implantable coil via an external coil. The external portions can be worn hung from the ear as a so-called behind-the-ear ("BTE") device, or in the ear canal as a so-called in-the-ear ("ITE") device (like a traditional acoustic hearing aid). Devices that include a vibrating stimulator or a loud speaker are also contemplated, as are hybrid devices that include a number of different stimulation systems. The corresponding stimulus can be in the form of electrical signals or mechanical actuations. For clarity, however, the technologies disclosed herein will be generally described in the context of cochlear implants.

Figure 1:
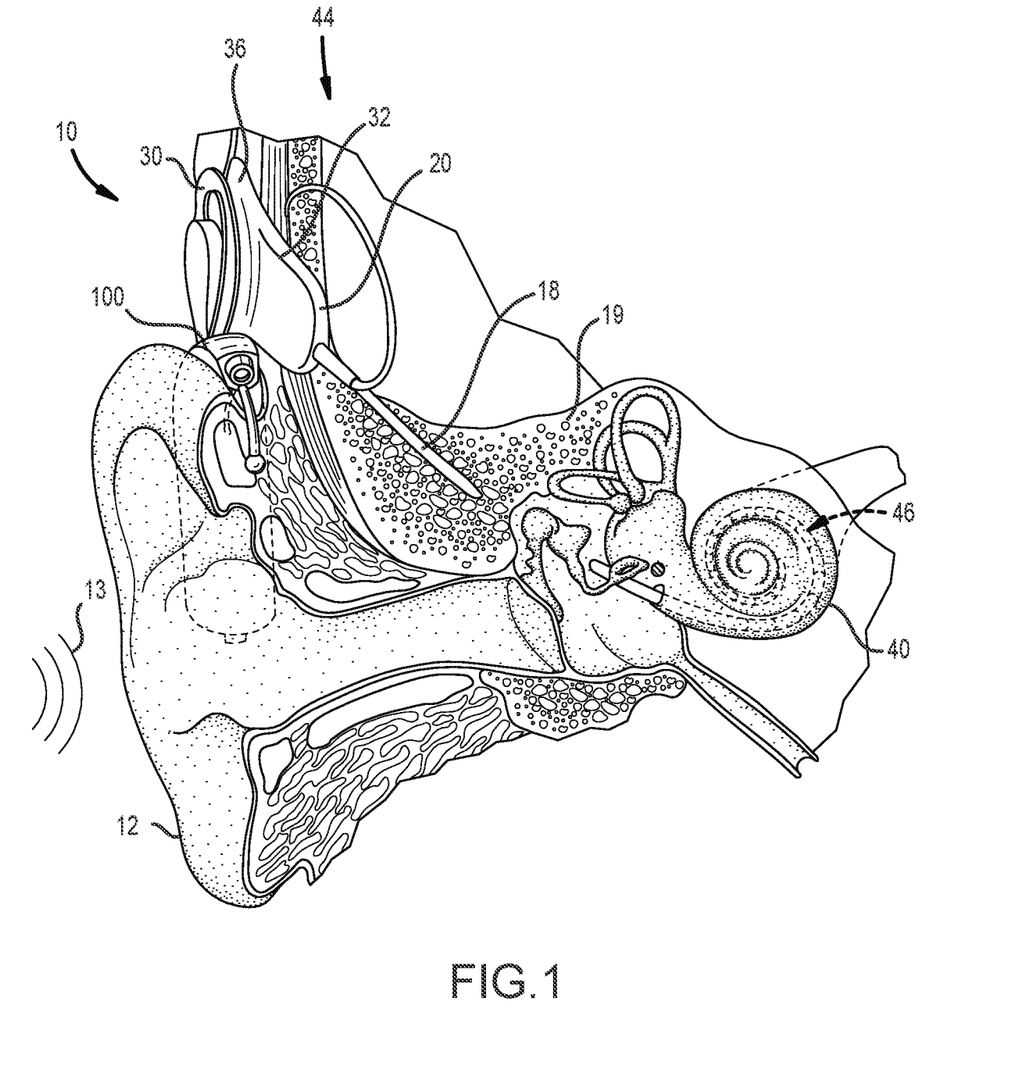
FIG. 1 is a partial view of an auditory prosthesis worn on a recipient.

Referring to FIG. 1, cochlear implant system 10 includes an implantable component 44 typically having an internal or implantable receiver/transceiver unit 32, a stimulator unit 20, and an elongate lead 18. The internal receiver/transceiver unit 32 permits the cochlear implant system 10 to receive signals from (and/or transmit signals to) an external device 100. The internal receiver/transceiver unit 32 includes an internal or implantable coil 36, and a magnet (not shown) fixed relative to the internal coil 36.

The received signals generally correspond to external sound 13. Internal receiver unit 32 and stimulator unit 20 are hermetically sealed within a biocompatible housing, sometimes collectively referred to as a stimulator/receiver unit. The magnets facilitate the operational alignment of the external and internal coils, enabling internal coil 36 to receive power and stimulation data from external coil 30. The external coil 30 is contained within an external portion attached to a head of a recipient. Elongate lead 18 has a proximal end connected to stimulator unit 20, and a distal end implanted in cochlea 40. Elongate lead 18 extends from stimulator unit 20 to cochlea 40 through mastoid bone 19.

In certain examples, external coil 30 transfers electrical signals (e.g., power and stimulation data) to internal coil 36 via a radio frequency (RF) link, as noted above over a closely coupled inductive coil link. Internal coil 36 is typically a wire coil comprised of multiple turns of electrically insulated single-strand or multi-strand platinum or gold wire. The electrical insulation of internal coil 36 is provided by a flexible silicone molding. Various types of energy transfer, such as electromagnetic, capacitive and inductive transfer, can be used to transfer the power and/or data from external device to cochlear implant. Several configurations of external and internal coils are described in further detail herein.

There are a variety of types of intra-cochlear stimulating assemblies including short, straight and peri-modiolar. Stimulating assembly 46 is configured to adopt a curved configuration during and or after implantation into the recipient's cochlea 40. To achieve this, in certain arrangements, stimulating assembly 46 is pre-curved to the same general curvature of a cochlea 40. Such examples of stimulating assembly 46, are typically held straight by, for example, a stiffening stylet (not shown) or sheath which is removed during implantation, or alternatively varying material combinations or the use of shape memory materials, so that the stimulating assembly can adopt its curved configuration when in the cochlea 40. Other methods of implantation, as well as other stimulating assemblies which adopt a curved configuration, can be used.

Stimulating assembly can be a peri-modiolar, a straight, or a mid-scala assembly. Alternatively, the stimulating assembly can be a short electrode implanted into at least in basal region. The stimulating assembly can extend towards apical end of cochlea, referred to as cochlea apex. In certain circumstances, the stimulating assembly can be inserted into cochlea via a cochleostomy. In other circumstances, a cochleostomy can be formed through round window, oval window, the promontory, or through an apical turn of cochlea.

Speech processing components, such as microphones, speech processing hardware and software, and other elements, can be disposed within a housing separate from the implantable portion of the auditory prosthesis. In certain examples, such components can be contained in an external portion that also includes the external coil described above. In another example, the sound processing components can be contained within a BTE device, such as BTE 100 depicted in FIG. 1. In the latter case, signals from the sound processing components are sent to an external portion containing the external coil.

Figure 2A:
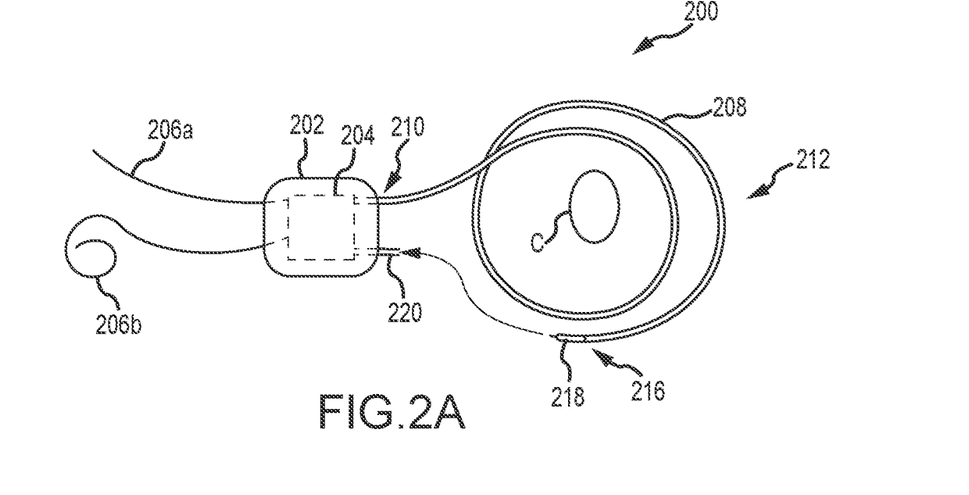
FIGS. 2A and 2B are schematic top views of an implantable portion of an auditory prosthesis in accordance with an example of the proposed technology.
Figure 2B:
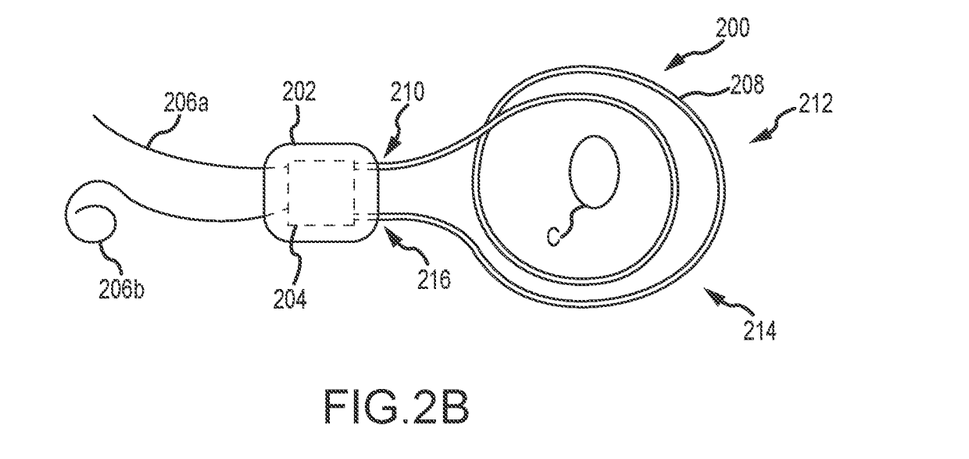

FIGS. 2A and 2B are schematic top views of an implantable portion 200 of an auditory prosthesis in accordance with an example of the proposed technology, and are described simultaneously. The implantable portion 200 includes a housing 202 typically of silicone or other biocompatible material. A stimulator unit 204 is disposed therein and generates a stimulus (e.g., an electrical signal) to be delivered to the cochlea. The stimulator unit 204 is connected to one or more transmission elements such as electrodes 206a, 206b that extend therefrom. The electrodes 206a, 206b are utilized to transmit or conduct the electrical stimulus signals to the cochlea. As described above, cochlear implants also typically include a coil and a magnet disposed in the housing 202. In the depicted example, however, a flexible wire 208 that functions as the coil is disposed outside the housing 202. In an example, the wire 208 can be gold doped in calcium.

Moreover, in certain examples, a magnet need not be utilized. In a significant deviation from known systems, the flexible wire 208 is connected at a first end 210 to the stimulator unit 204. As part of the implantation procedure, the implantable portion 204 is implanted proximate the ear canal, as known to persons of skill in the art. The flexible wire 208 is routed about the ear canal C to form one or more loops 212 that, once the loops 212 are completed, form a receiver coil 214. To ease implantation and guiding of the wire 208, a second end 216 can include a needle 218, which a surgeon can use to guide the wire 208 around the ear canal C using forceps or other instruments. Once the desired number of loops 212 are made about the ear canal C, the needle 218 acts as a connector and is connectable to a port 220 in the stimulator unit 204 and the housing 202. Once detachably received in the port 220, the completed implantable coil 214 is formed. Any number of loops 212 can be made about the ear canal C, as required or desired for a particular application. In certain examples, a greater number of loops 212 can be utilized to form a coil 214 having greater quality of signal transmission/reception.

Figure 2C:
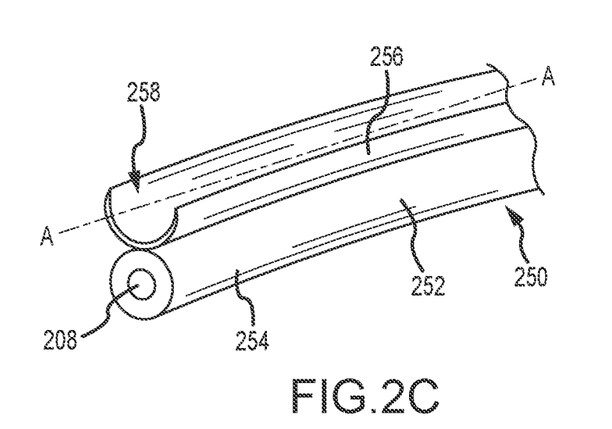
FIGS. 2C and 2D depict partial schematic views of a wire bundling system in accordance with an example of the proposed technology.
Figure 2D:
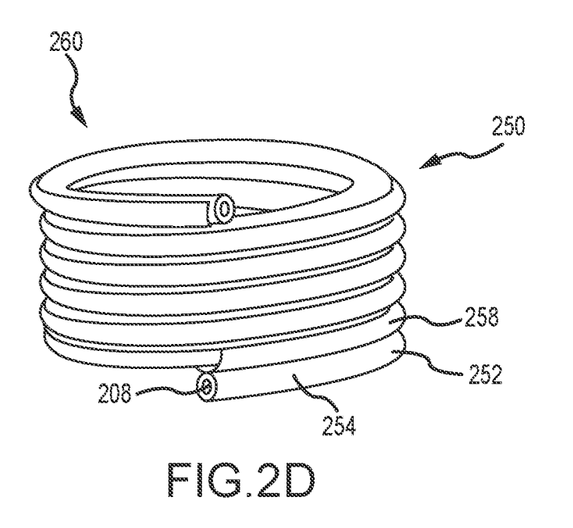

The examples depicted in FIGS. 2A and 2B depict loose loops 212 of the wire 208 that form the coil 214. However, it can be advantageous that the loops 212 are disposed close to each other so as to improve signal transmission and reception. In that regard, FIGS. 2C and 2D depict a wire bundling system 250 in accordance with an example of the proposed technology and are described simultaneously. A wire 208 is surrounded by a silicone or other resilient, flexible sheath or sleeve 252 that electrically insulates. Additionally, the sleeve 252 can be stretchable and the wire 208 can have a wave-like configuration so as to lengthen as the sleeve 252 is stretched. The sleeve 252 includes a body 254 in which the wire 208 is disposed. Secured to or integral with the body 254 is a U-shaped bracket 256. The U-shaped bracket 256 defines a channel 258 sized to receive the body 254 as it is looped during implantation. During implantation, a first loop about the ear canal C is made as described above. Thereafter, an end of the body 254 is inserted into the U-shaped bracket 256 and advanced substantially parallel within an axis A of the channel 258 until a bundle 260 having the desired number of closely-disposed loops is formed. An interior surface of the U-shaped bracket 256 can be coated with a low-friction coating to ease sliding insertion of the body 254 therein.

Figure 3:
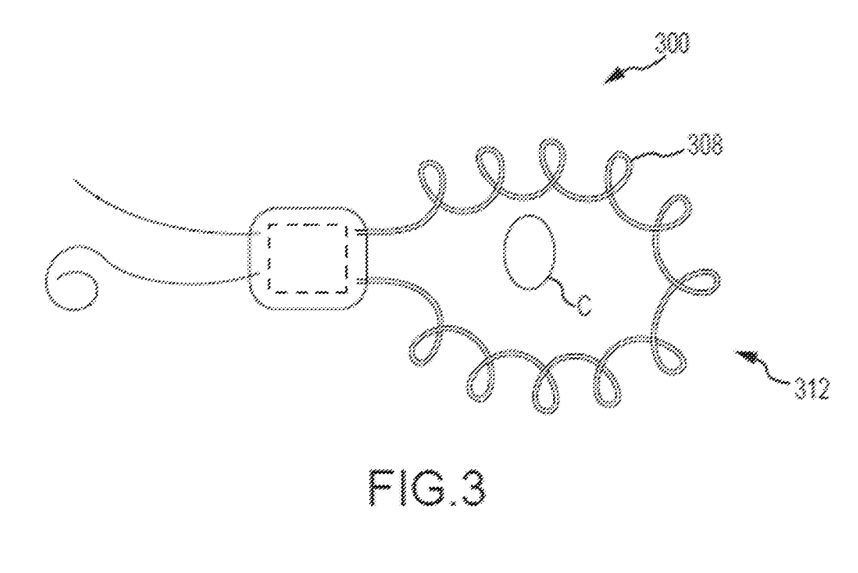
FIG. 3 is a schematic top view of an implantable portion of an auditory prosthesis in accordance with another example of the proposed technology.

FIG. 3 is a schematic top view of an implantable portion 300 of an auditory prosthesis in accordance with another example of the proposed technology. A number of the elements are described above with regard to FIGS. 2A and 2B and are not necessarily described further. These elements are numbered consistently with those of FIGS. 2A and 2B, but beginning with 300. Here, the wire 308 is configured in a helical shape, which can provide greater flexibility during implantation of the wire 308, and can also improve signal transmission/reception quality. As with the examples depicted elsewhere herein, one or more loops 312 about the ear canal C can be made.

Figure 4A:
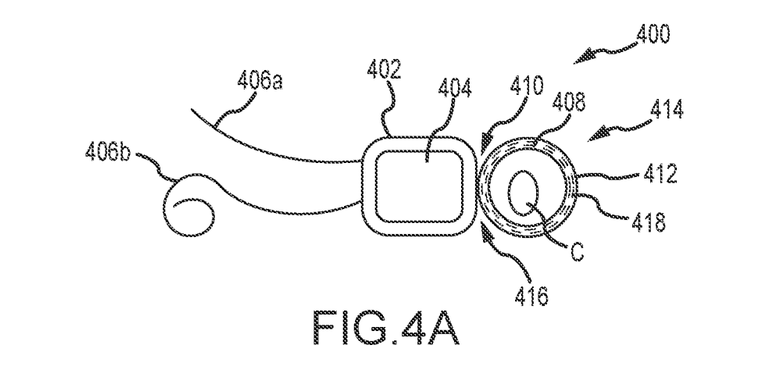
FIGS. 4A and 4B are schematic top and section views of an implantable portion of an auditory prosthesis in accordance with another example of the proposed technology.
Figure 4B:
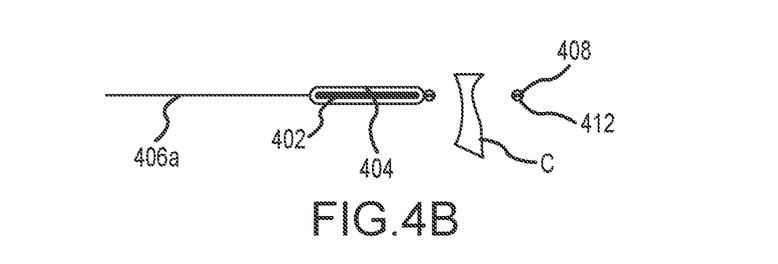

FIGS. 4A and 4B are schematic top and section views of an implantable portion 400 of an auditory prosthesis in accordance with another example of the proposed technology. FIGS. 4A and 4B are described simultaneously along with FIG. 4C, which depicts a partial enlarged top view of the implantable portion 400. A number of the elements are described above with regard to FIGS. 2A and 2B and are not necessarily described further. These elements are numbered consistently with those of FIGS. 2A and 2B, but beginning with 400. A first end 410 of a wire 408 is connected to and extends from a stimulator unit 404 and makes a number of turns or partial loops 412 in a generally circular pattern before terminating at a second end 416. This circular pattern of curved wire 408 forms a substantially circular coil 414. At the second end 416, the wire 408 terminates at a connector 418a. The loops 412 can optionally be disposed within a flexible sleeve 418 which can be manufactured from the same material as the housing 402 (e.g., silicone) and in certain examples is integral therewith. The sleeve 418 can be biased into a predefined orientation (e.g., curved) so it can more easily encircle the ear canal C during implantation. A biasing element 422 can include a wire or elastic element within or on the sleeve 418 that urges the sleeve 418 into a predefined configuration.

Figure 4C:
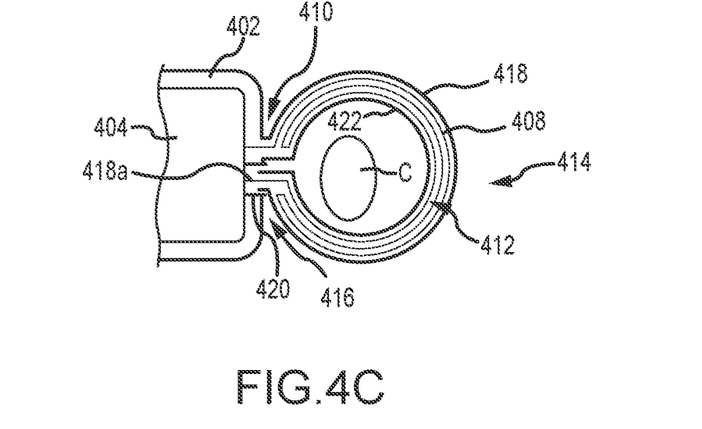
FIG. 4C depicts a partial enlarged schematic top view of the implantable portion of FIGS. 4A and 4B.

Once disposed completely around the ear canal C, the connector 418a can be inserted into a mating port 420 in the housing 402 and connected to stimulator unit 404. A seal can be formed between the sleeve 418 and the port 420, e.g., with a friction fit, snap connector, adhesive, or combinations thereof. Once connected, the sleeve 418 forms an annulus with an open central portion. In another example, the wire 408 and sleeve 418 can be permanently connected at the stimulator unit 404.

As described above, certain examples of implantable portions depicted herein do not utilize a magnet. This has significant advantages in that the implantable portion can still be worn by the recipient during a magnetic resonance imaging (MRI) or other procedure that would typically require removal of the implantable portion and/or magnet. Typically, magnets in the implantable portion and in the external portion of the auditory prosthesis interact so as to hold the external portion proximate the implantable portion to ensure proper signal transmission between the implantable coil and external coil.

Absence of magnets, therefore, can cause signal transmission problems between the implantable portion and the external portion. The disclosed technologies address this and other problems by disposing the external transmission coil proximate the area of implantation of the implantable coil, and utilize body parts (e.g., the pinna or the ear canal) to ensure the implantable and external coils remain proximate each other when the external portion is disposed in or proximate the head.

Figure 5A:
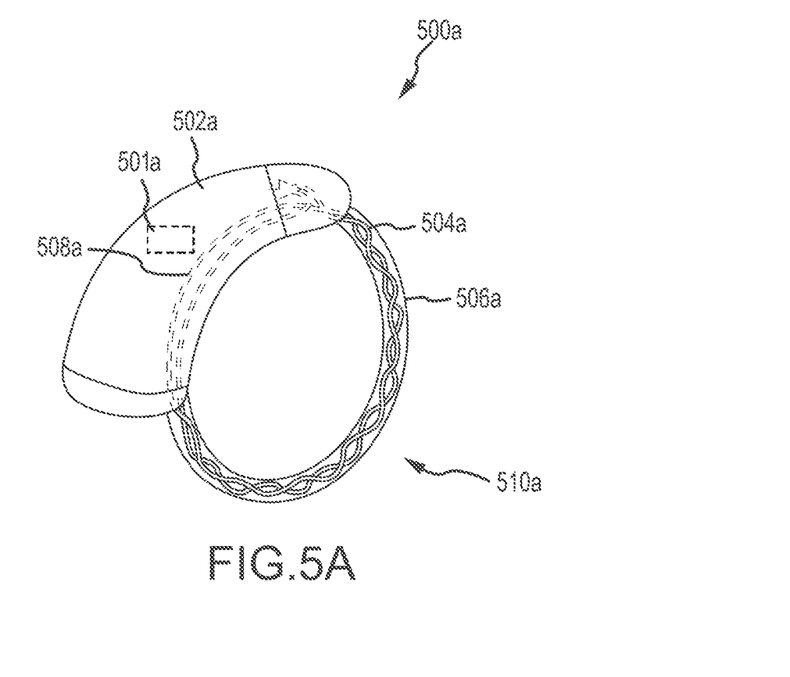
FIGS. 5A-5C are schematic side views of external portions of auditory prostheses in accordance with examples of the proposed technology.
Figure 5B:
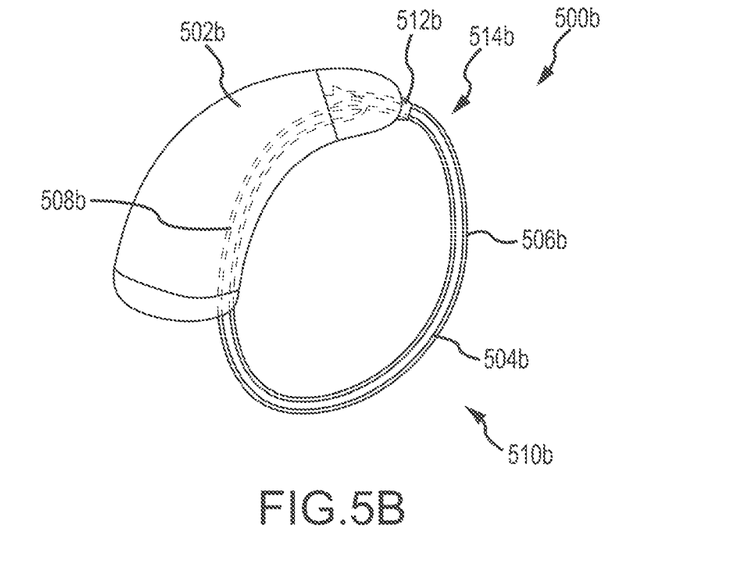
Figure 5C:
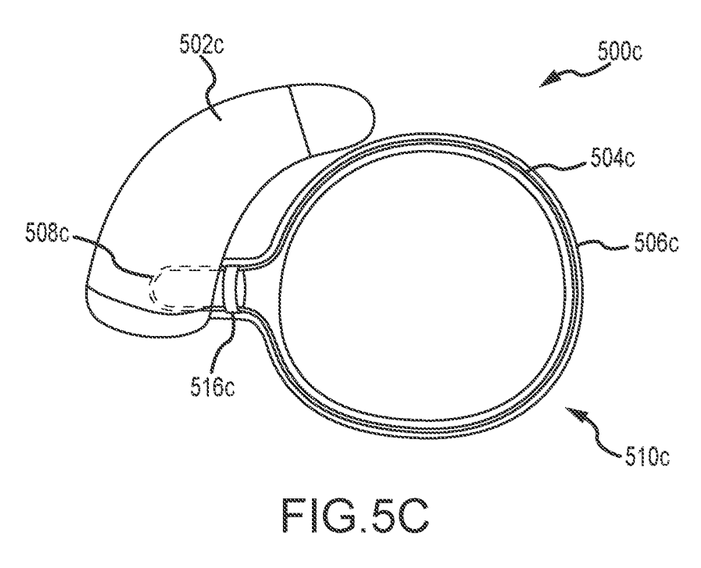

FIGS. 5A-5C are schematic side views of external portions of auditory prostheses 500a-500c in accordance with examples of the proposed technology. In FIG. 5A, the auditory prosthesis 500a includes a housing 502a, in this case in the form factor of a BTE device. The BTE device 500a includes a sound processor 501a, as well as microphones, batteries, and other components described herein, which are not depicted in FIG. 5A. The BTE device 500a includes a wire or lead 504a extending therefrom. In the depicted example, the wire 504a is a twisted radio frequency (RF) coil that adapts to the circumference of the pinna. The wire 504a can be disposed in a flexible (e.g., silicone) sleeve 506a for comfort when in contact with the pinna of the recipient. The sleeve 506a can be substantially transparent or flesh-colored to disguise the appearance thereof. An oval shape can help further disguise the sleeve 506a. In other examples, circular, crescent, or other shapes can be utilized. The wire 504a can be configured to straighten within the silicone sleeve 506a, so as to more comfortably stretch to fit the recipient, regardless of pinna size. A portion 508a of the wire 504a is disposed within the housing 502a, to form a complete coil 510a. In FIG. 5B, an auditory prosthesis 500b includes a housing 502b and a wire 504b having at least a portion 508b disposed therein. The wire 504b includes a connector 512b that connects a second end 514b of the wire 504b to the housing 502b, so as to form a complete coil 510b. As above, the wire 504b can be disposed within a silicon sleeve 506b, if required or desired. In this example, after the BTE device 500b is placed on the pinna, the wire 504b and sleeve 506b can be looped around the pinna and connected to the housing 502b with a connector 512b, thus forming the coil 510b. In FIG. 5C, an auditory prosthesis 500c includes a housing 502c and a wire 504c having at least a portion 508c disposed therein. The wire 504c includes an elastic ring 516c that can be used to tighten the coil 510c around the pinna. As above, the wire 504c can be disposed within a silicon sleeve 506c.

Figure 6A:
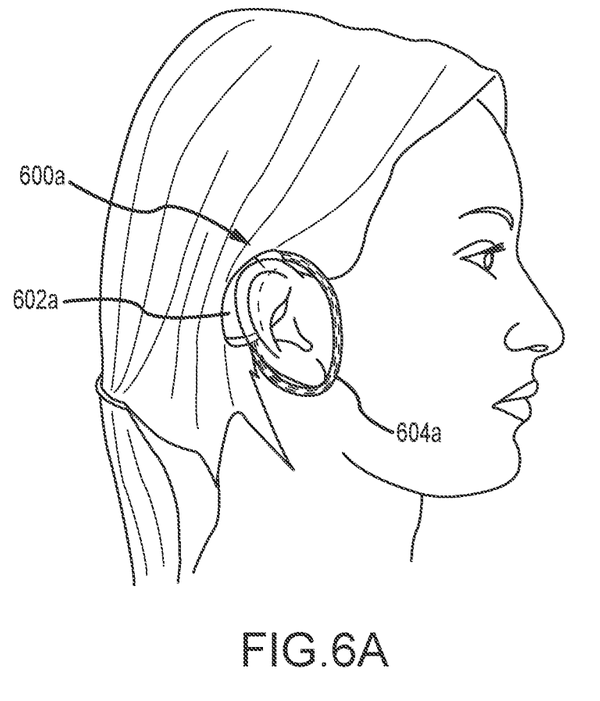
FIGS. 6A-6C depict examples of external portions of auditory prostheses worn by a recipient.
Figure 6B:
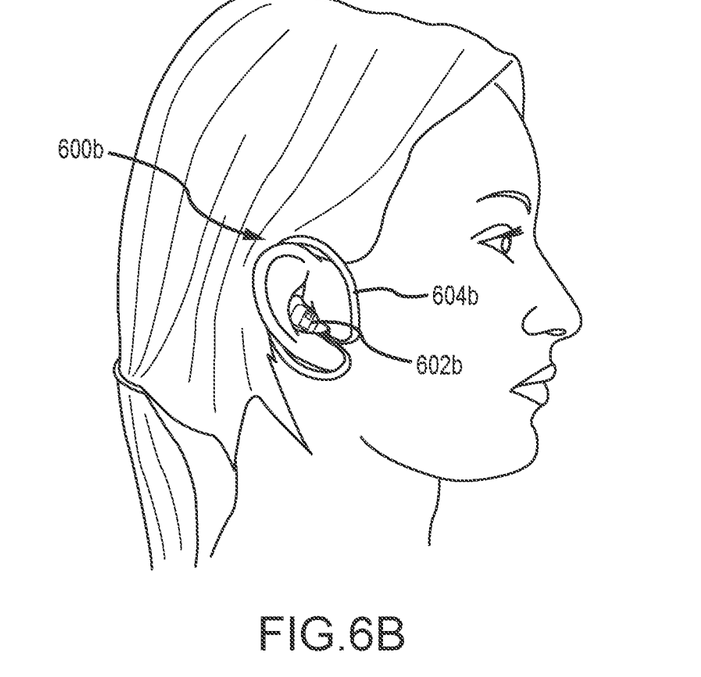
Figure 6C:
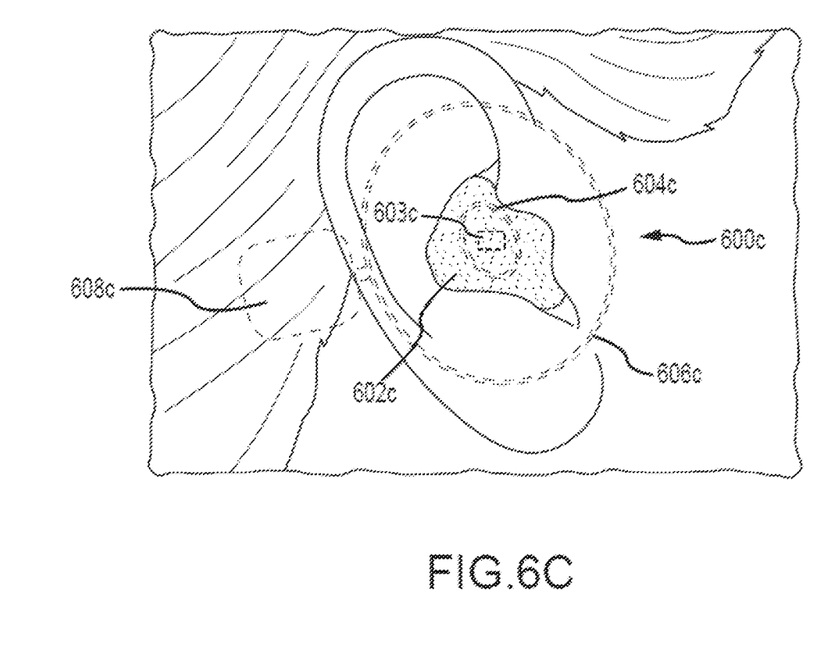

FIGS. 6A-6C depict examples of external portions of auditory prostheses 600a-600c worn by a recipient. In FIG. 6A, the auditory prosthesis includes an external portion having a housing 602a worn behind the ear (as a BTE device) and a coil 604a disposed about the pinna. In FIG. 6B, the auditory prosthesis has a housing 602b configured to fit within the ear canal (as an ITE device). An external coil 604b is connected to the housing 602b and extends around the pinna. In FIG. 6C, the housing 602c of the auditory prosthesis 600c is configured to fit within the ear canal (again, as in an ITE device). The housing 602c contains a transceiver 603c that communicates, via an external coil 604c, with an implantable coil 606c disposed about the ear canal, as described elsewhere herein. The implantable coil 606c is connected to a stimulator unit 608c, such as those depicted above.

Figure 7A:
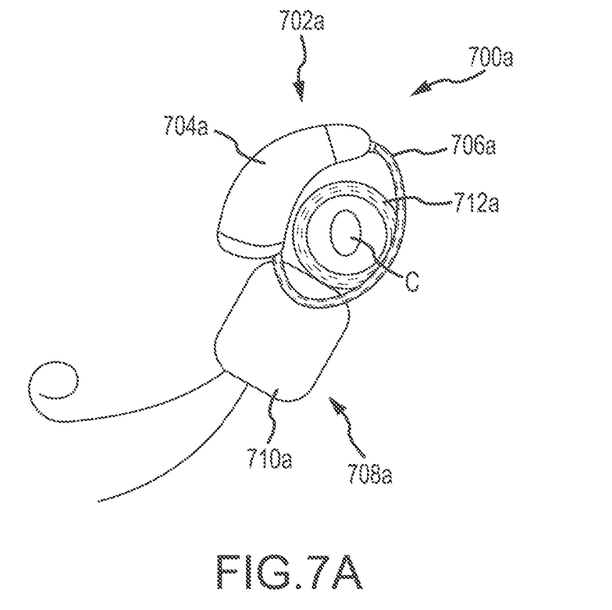
FIGS. 7A-7C depict examples of auditory prostheses worn by a recipient.
Figure 7B:
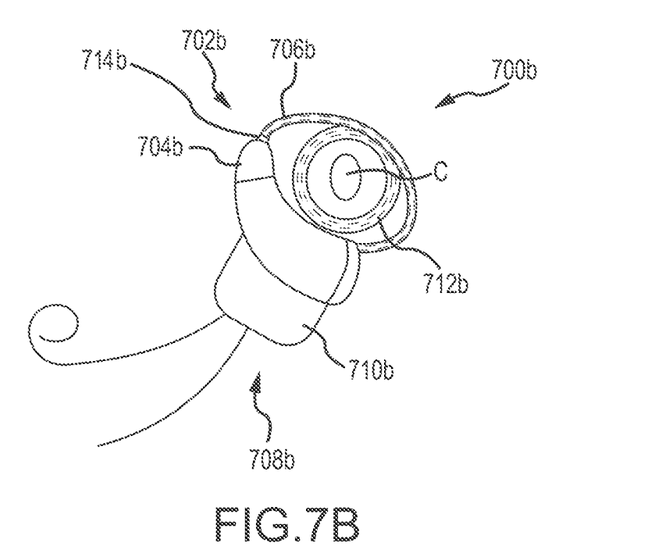
Figure 7C:
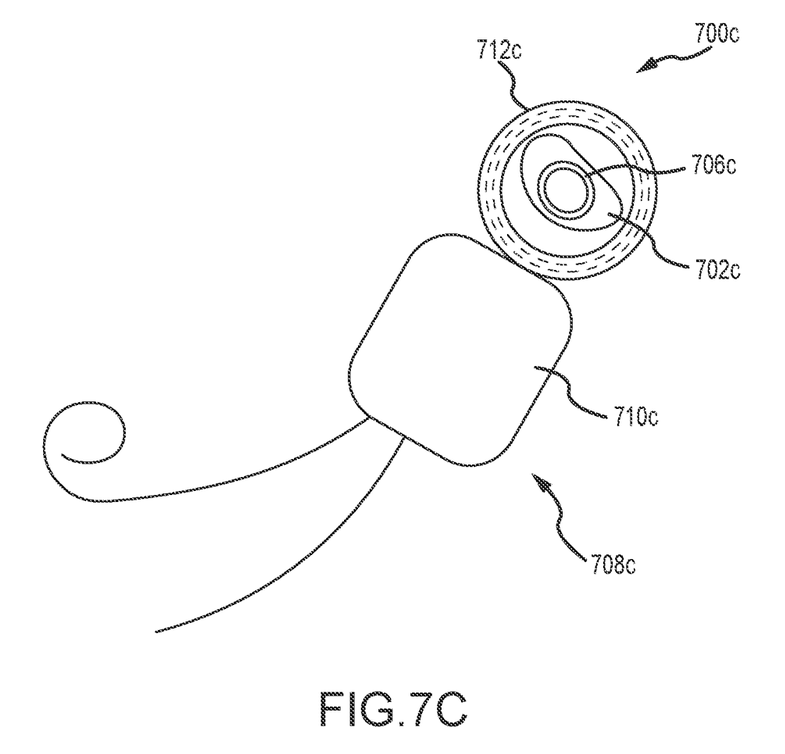

FIGS. 7A-7C depict examples of auditory prostheses 700a-700c worn by a recipient. The relative positions of the various components and the ear canal C are depicted and described in more detail herein. In FIG. 7A, the auditory prosthesis 700a includes an external portion 702a in the form of a BTE device housing 704a. A coil 706a sized to encircle the pinna is connected to the BTE device housing 704a, for example in one of the configurations depicted herein. An implantable portion 708a is a cochlear implant having a housing 710a containing a stimulator unit. A coil 712a is disposed about the ear canal C. Given the proximity of the coils 706a, 712a, signals can be communicated therebetween so as to cause a stimulus to be sent to a recipient of the auditory prosthesis 700a.

In FIG. 7B, the auditory prosthesis 700b includes an external portion 702b in the form of a BTE device housing 704b. Here, the BTE device housing 704b is configured so as to be worn low on the pinna. This can be desirable because it allows the BTE device housing 704b to be at least partially hidden by the ear lobe. Additionally, one or more microphones 714b can be disposed on a forward-facing surface of the BTE device housing 704b, which can improve sound reception. A coil 706b sized to encircle the pinna is connected to the BTE device housing 704b, for example in one of the configurations depicted herein. An implantable portion 708b is a cochlear implant having a housing 710b containing a stimulator unit. A coil 712b is disposed about the ear canal C. Given the proximity of the coils 706b, 712b, signals can be communicated therebetween so as to cause a stimulus to be sent to a recipient of the auditory prosthesis 700b.

In FIG. 7C, the auditory prosthesis 700c includes an external portion 702c in the form of a ITE device housing 704c. Here, the ITE device housing 704c is configured so as to be disposed within the ear canal (not shown here). A coil 706c is disposed within the ITE device housing 704c, thus providing a very non-obtrusive option for recipient who may desire the discretion of a more traditional hearing aid. An implantable portion 708c is a cochlear implant having a housing 710c containing a stimulator unit. A coil 712c is disposed about the ear canal. Given the proximity of the coils 706c, 712c, signals can be communicated therebetween so as to cause a stimulus to be sent to a recipient of the auditory prosthesis 700c.

Figure 8:
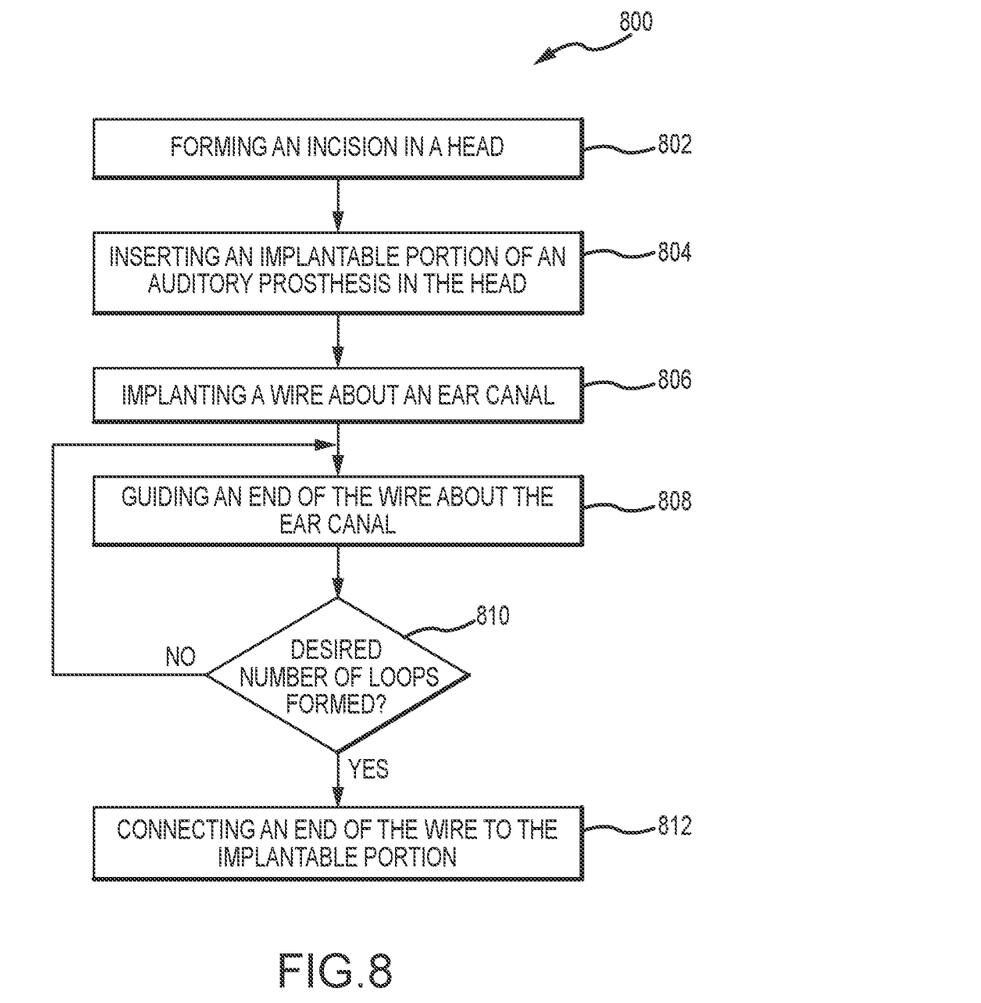
FIG. 8 depicts a method of implanting an implantable portion of an auditory prosthesis.

FIG. 8 depicts a method 800 of implanting an implantable portion of an auditory prosthesis. The method 800 begins at operation 802 where an incision is formed in the head of a recipient, proximate the pinna. At operation 804, an implantable portion of an auditory prosthesis is inserted into the incision. As described elsewhere herein, the implantable portion can be a cochlear implant, direct acoustic stimulator, or other implantable portion of an auditory prosthesis. At operation 806, a wire is implanted about the ear canal so as to form a coil. Operation 808 describes an example implantation of the wire which can include guiding an end of the wire about the ear canal. In decision 810, it is determined if a desired number of loops are formed. If the desired number of loops are not formed, flow returns to operation 808. If the desired number of loops have been formed, flow continues to operation 812. Of course, certain examples of implantable devices described herein require only a single loop about the ear canal (e.g., the sleeve and wire combination of FIGS. 4A and 4B). Once the desired number of loops are formed, operation 812 describes connecting the end of the wire to the implantable portion. The incision can then be closed. Other coil implantation processes are contemplated. For example, the ear canal can be severed or the pinna can be at least partially removed so as to ease implantation. In such an example, an implantable portion similar to the type depicted in FIGS. 4A-4C can be utilized. Such an example would have a wire 408 and a sleeve 418 permanently connected at both ends thereof to the stimulator unit 404. Once the ear canal and/or pinna have been severed, or partially removed, the annular sleeve 418 can be placed around the ear canal, and then the severed/removed anatomy can be reattached.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific aspects are described herein, the scope of the technology is not limited to those specific examples. One skilled in the art will recognize other examples or improvements that are within the scope of the present technology. Therefore, the specific structure, acts, or media are disclosed only as illustrative examples. The scope of the technology is defined by the following claims and any equivalents therein.

The invention claimed is:

1. A medical device, comprising:
a housing comprising a port; and
an implantable wire comprising a first end extending from the housing and a second end configured to detachably couple to the port of the housing, wherein the implantable wire is configured to be guided into one or more loops to form a first coil configured to communicate with a second coil.

2. The medical device of claim 1, comprising a stimulator unit disposed in the housing, wherein the implantable wire is configured to detachably couple to the port of the housing to couple to the stimulator unit.

3. The medical device of claim 1, comprising:
an input device configured to receive an environmental signal;
a processor configured to convert the environmental signal into an output signal, and
wherein the second coil is configured to transmit the output signal to the first coil.

4. The medical device of claim 3, wherein the implantable wire is disposed around an ear canal of a recipient, and the second coil is external to the recipient.

5. The medical device of claim 4, wherein the second coil is at least partially positioned in the ear canal.

6. The medical device of claim 1, wherein the implantable wire comprises a connector at the second end, and wherein the connector is configured to insert into the port of the housing to detachably couple to the port.

7. The medical device of claim 1, comprising a sleeve surrounding the implantable wire to insulate the implantable wire.

8. A method, comprising:
implanting a housing of a device into a recipient, wherein the device comprises a wire connected to the housing at a first end of the wire;
guiding the wire into one or more loops; and
connecting a second end of the wire to the housing.

9. The method of claim 8, wherein the device further comprises a bracket, and wherein the method further comprises inserting the wire along the bracket to guide the wire into the one or more loops.

10. The method of claim 8, wherein guiding the wire into the one or more loops comprises wrapping the wire around an ear canal of the recipient.

11. The method of claim 8, wherein the housing comprises a port, and wherein connecting the second end of the wire to the housing comprises inserting the second end of the wire into the port.

12. The method of claim 8, comprising disposing an external coil around a pinna of the recipient, wherein the external coil is configured to communicate with the wire.

13. The method of claim 8, wherein the device comprises a stimulator unit disposed in the housing, and wherein connecting the second end of the wire to the housing comprises coupling the wire to the stimulator unit.

14. A device, comprising:
a housing;
a wire comprising a first end extending from the housing and a second end having a connector configured to couple to the housing; and
a flexible sleeve connected to the housing, wherein the wire is disposed in the flexible sleeve, and wherein the flexible sleeve is configured to guide the wire into one or more loops.

15. The device of claim 14, further comprising a bracket, wherein the flexible sleeve is configured to be disposed in and moved along the bracket, and wherein the bracket is configured to cause the wire to curve during movement along the bracket to guide the wire into the one or more loops.

16. The device of claim 14, further comprising a biasing element configured to urge the flexible sleeve to curve to guide the wire into the one or more loops.

17. The device of claim 16, wherein the biasing element comprises an elastic element disposed within the flexible sleeve.

18. The device of claim 14, wherein the one or more loops of the wire surround an ear canal of a recipient of the device.

19. The device of claim 14, wherein the one or more loops of the wire form a first coil configured to communicate power and/or data to a second coil.

20. A system, comprising:
an implant comprising a wire wrapped around an ear canal of a recipient;
an external coil configured to communicate with the wire wrapped around the ear canal; and
a housing, wherein the wire comprises a first end and a second end that are each connected to the housing, and wherein the wire forms one or more loops between the first end and the second end, each of the one or more loops being wrapped around the ear canal of the recipient.

21. The system of claim 20, wherein the external coil is configured to wrap around a pinna of the recipient.

22. The system of claim 20, wherein the implant comprises a stimulator unit coupled to the wire, and the external coil is configured to communicate with the wire to cause the stimulator unit to provide a stimulus to the recipient.

23. The system of claim 20, wherein the external coil comprises an additional housing, a first portion extending into the additional housing, and a second portion extending out of the additional housing.

24. The system of claim 20, wherein the wire of the implant extends helically to form the one or more loops, and the one or more loops cooperatively wrap around the ear canal.

* * * * *